United States Patent [19]

Isa et al.

[11] 3,947,509

[45] Mar. 30, 1976

[54] METHOD FOR PREPARATION OF HYDROCARBON LIQUID POLYMERS

[75] Inventors: Hiroshi Isa; Toshiyuki Ukigai, both of Yachiyo; Anri Tominaga, Tokyo; Ryozo Taniyasu, Narashino; Masuzo Nagayama, Tokyo, all of Japan

[73] Assignee: Lion Fat & Oil Co., Ltd., Tokyo, Japan

[22] Filed: Feb. 14, 1975

[21] Appl. No.: 549,864

[30] Foreign Application Priority Data

Feb. 22, 1974  Japan.................................. 49-20476

[52] U.S. Cl........ 260/676 R; 252/59; 260/683.15 B; 260/683.9
[51] Int. Cl.²...................... C07C 9/00; C10M 1/16
[58] Field of Search.......... 260/683.15 B, 683.15 D, 260/676, 683.9; 252/59

[56] References Cited
UNITED STATES PATENTS

| | | | |
|---|---|---|---|
| 2,384,916 | 9/1945 | Holmes | 260/683.15 B |
| 2,697,694 | 12/1954 | Shalit et al. | 252/59 |
| 3,024,293 | 3/1962 | Nelson et al. | 260/683.15 B |
| 3,833,678 | 9/1974 | Brennan | 260/683.15 B |

*Primary Examiner*—Delbert E. Gantz
*Assistant Examiner*—Juanita M. Nelson
*Attorney, Agent, or Firm*—Woodhams, Blanchard and Flynn

[57]  ABSTRACT

A method of effecting polymerization of olefins having 6 or more carbon atoms or mixtures of such olefins (hereinafter referred to as the feed olefin), to produce a hydrocarbon liquid polymer which comprises mixing a catalyst composed of aluminum chloride, ketone having 4 or more carbon atoms and olefin catalyst constituent with 0.01 to 0.3 mole of ester, ether or alcohol per mole of said aluminum chloride and effecting the polymerization of the feed olefin at a reaction temperature of more than 60°C.

14 Claims, No Drawings

METHOD FOR PREPARATION OF HYDROCARBON LIQUID POLYMERS

BACKGROUND OF THE INVENTION a. Field of the Invention

The present invention relates to a method of producing a hydrocarbon liquid polymer, and to be precise, it relates to a method of obtaining a liquid polymer having a high viscosity index, low pour point and very low viscosity by effecting the polymerization of a feed olefin having more than 6 carbon atoms in the presence of a specific catalyst.

b. Description of the Prior Art

The currently available lubricating oils can be broadly classified into the petroleum lubricating oils, synthetic lubricating oils, fatty oils, etc. on the basis of the starting material used for manufacturing thereof, but with the recent increase of the range of use of these lubricating oils, the fields needing lubricating oils with properties meeting the requirements of high viscosity index, low pour point, etc. are increasing. For instance, in the fields where the heat resisting property and low-temperature stability are required of gas turbine oil, refrigerating machine oil, etc. or in fields where the gear oil, motor oil, grease, etc. are required to be free of constant maintenance work, the demand for such lubricating oils has increased. However, the petroleum lubricating oils — which have the widest range of application at present and are usually obtained from petroleum — do not have all of such properties as above to perfection as required for said specific use.

On the other hand, among the synthetic lubricating oils produced by organic synthesizing methods, the liquid polymers or olefin polymer oils to be obtained by polymerizing olefins have recently become the object of public attention. And, as the method for the polymerization of olefins, the cationic polymerization method employing Lewis acids like aluminum chloride and the radical polymerization method employing heat or peroxides are popular. However, the polymerizations by these conventional methods are accompanied by isomerization during the reaction, and in fact, there has not yet been obtained a polymerized oil having as high a viscosity index as is required. Under such circumstances, in the production of olefin polymer oils, the application of the so-called Ziegler catalyst which is a coordinated anionic catalyst and is capable of effecting regular polymerization is nowadays in the limelight, and various polymerization reactions employing varieties of olefins as raw material have been tried: for instance, the application of a complex compound prepared from monoethylene aluminum dichloride and titanium tetrachloride as catalyst in polymerizing olefins having 6 to 10 carbon atoms has proved effective for producing liquid polymers having tolerably superior properties, such that the viscosity index is more than 130, the flash point is more than 210°C and the pour point is less than −50°C.

However, said Ziegler catalyst is defective in that (1) the active ingredient of this catalyst is unstable so that it is difficult to recover it for reuse, (2) the catalyst per se is expensive, (3) the handling of the catalyst is attended with danger so that it is necessary to take intensive safety measures, and (4) it is difficult to synthesize a polymerized oil having low grade of viscosity and high efficiency by the use of this kind of catalyst.

Polymerized oils with low grade of viscosity are especially important as they have a wide range of application as gas turbine oil, working oil for aircraft and substitute for squalene, and accordingly, various improvements thereof have been tried. Nevertheless, as there has not been found any apposite catalyst to date, it is usual to prepare a polymerized oil with relatively high viscosity by the use of a Ziegler catalyst, fractionate said polymerized oil by molecular distillation or the like, and employ a portion of the resulting fractions. But, the yield of the fraction having the required properties is no more than 30 to 40%, and as long as the residual fractions equivalent to 60 to 70% are not utilized effectively, this measure cannot be called an effective method. Accordingly, there has been a demand for the development of such a catalyst as will render it possible to produce polymerized oils with low grade of viscosity through mere polymerization.

In this connection, there have admittedly been some attempts to recover the applied catalyst for reuse. For instance, Japanese Patent publication No. 3804/1969 discloses a method comprising dissolving excess aluminum chloride in a complex composed of aluminum chloride and ethyl acetate ester, effecting the polymerization of olefin by the use of the resulting solution, separating the catalyst by settling, and recovering the thus separated catalyst for reuse. U.S. Pat. No. 2697694 discloses a method of obtaining a macromolecular polybutene, which comprises dissolving excess aluminum chloride in a mixture of aluminum chloride and acetone and effecting the polymerization of isobutane by the use of the resulting solution, and in the case of this method too, the applied catalyst is recovered for reuse in the same way as in the foregoing method. However, both of these methods are alike in the application of the cationic polymerization employing aluminum chloride, and neither of them can produce a polymer of olefin having a relatively low viscosity and high viscosity index.

SUMMARY OF THE INVENTION

One object of the present invention is to provide a method of producing a hydrocarbon liquid polymer having a high viscosity index, low pour point and very low viscosity. Another object of the present invention is to provide a method of producing a hydrocarbon liquid polymer which is satisfactory as a substitute for lubricating oils and squalene, at a high yield without resorting to fractional distillation or like operations. A further object of the present invention is to provide a method of easily separating a polymerization catalyst from a hydrocarbon liquid polymer.

As a result of a series of experiments and examinations aiming at the preparation of a hydrocarbon liquid polymer having highly advantageous properties as set forth above, the present inventors have come to the finding that an extremely satisfactory hydrocarbon liquid polymer can be obtained by effecting the polymerization of a feed olefin having 6 or more carbon atoms in the presence of a mixture consisting of a catalyst ingredient prepared from (a) aluminum chloride, (b) ketone having 4 or more carbon atoms and (c) an olefin catalyst constituent and a specific amount of (d) ester, ether or alcohol relative to said aluminum chloride (a) at a reaction temperature of more than 60°C. The present invention has been accomplished on the basis of this finding.

In other words, a method of producing a hydrocarbon liquid polymer under the present invention is characterized in that, at the time of effecting the lower polymerization of olefins having 6 or more carbon atoms or mixtures of such olefins (to wit, the feed olefin), said polymerization of the feed olefin is effected at a reaction temperature of more than 60°C in the presence of a mixture consisting of a catalyst ingredient prepared from (a) aluminum chloride, (b) ketone having 4 or more carbon atoms and (c) olefin catalyst constituent and 0.01 to 0.3 mole of (d) ester, ether or alcohol per mole of said aluminum chloride (a).

As described above, the feed olefin for use in the present invention is α-olefin or inner olefin such as β-olefin, γ-olefin, etc. having 6 or more carbon atoms, and to give instances of applicable olefins, there are hexene-1, octene-3, tridecene-1, octadecene-2, as well as mixtures thereof. In order to obtain a polymer of satisfactory lubricating efficiency, the average carbon number of the feed olefin is preferably in the range of from 8 to 10.

The ketone (b) necessary for forming an active ingredient of catalyst is a linear ketone (for instance, aliphatic ketone and aromatic ketone) or cyclic ketone having 4 or more carbon atoms, and to give instances of applicable ketones, there are methyl ethyl ketone, diethyl ketone, diisobutyl ketone, dioctyl ketone, cyclohexanone, as well as analogues thereof. Acetone is undesirable because the content of enol therein is so small that the formation of the active ingredient of catalyst is difficult. As olefin catalyst constituent (c) necessary for forming the active ingredient of the catalyst, such olefins as propylene, butene, etc. which are different from the feed olefin are also applicable, but when the activity of catalyst and the properties of the liquid polymers to be obtained are taken into consideration, it is preferable to employ an olefin catalyst constituent similar to the feed olefin. The mixing ratio of aluminum chloride (a) to ketone (b) is preferably in the range of from 1.0:1.0 to 1.0:1.2 (molar ratio). In the case where aluminum chloride is above that range, the reaction becomes cationic polymerization, resulting in failure to obtain a liquid polymer (or polymerized oil) having low viscosity and high viscosity index, while in the case where the amount of ketone applied is more than 1.2 mol. per mole of aluminum chloride, the progress of the reaction is impeded. Accordingly, the optimum molar ratio is in the range of from 1.02 to 1.10 mole of ketone per mole of aluminum chloride. As for the amount of olefin catalyst constituent (c), it is required to be more than 1 mol. % relative to aluminum chloride (a). Further, as for the amount of aluminum chloride (a) as catalyst, it is desirable to be in the range of from 0.1 to 5 mole percent preferably from 1.0 to 3.0 mole percent, based on the feed olefin.

Among the substances applicable as the ingredient (d) to be added to the catalyst prepared from the ingredients (a), (b) and (c) at the time of activation of said catalyst, said ester is alkyl ester of fatty acid having less than 10 carbon atoms, such as methyl formate, ethyl formate, methyl octylate and ethoxy acetate (acetic cellulose), said ether is alkyl ether having less than 10 carbon atoms, such as diethyl ether, dibutyl ether and ethylene glycol, aand said alcohol is monohydric of polyhydric alcohol having less than 10 carbon atoms, such as methanol, ethanol, isobutanol, octanol, ethylene glycol, ethylene glycol monoethyl ether and glycerine. The appropriate amount of these ingredients (d) to be added is in the range of from 0.01 to 0.3 mole per mole of aluminum chloride: in the case where the amount of ingredient (d) is less than 0.01 mole, the effect of addition thereof is insufficient, while in the case where it is in excess of 0.3 mole, the progress of reaction is extremely impeded.

On the occasion of putting the method of the present invention into practice, it is preferable to prepare an active ingredient of catalyst from aluminum chloride (a), ketone (b), olefin catalyst constituent (c) and ether, ester or alcohol (d), and add it to the feed olefin thereby to polymerize the feed olefin. But, in view of the fact that the formation of said active ingredient of catalyst takes place even during the reaction, it also will do to dissolve aluminum chloride in a mixture solution of ketone and ester, ether or alcohol and then add the feed olefin to the resulting solution thereby to effect the polymerization. In this case, however, the addition of aluminum chloride afterwards may give rise to the concurrence of ordinary cationic polymerization, and therefore, care must be taken.

As to the reaction temperature, any temperature is applicable as far as it is more than 60°C; however, when it is more than 200°C, the viscosity index of the resulting polymerized oil tends to be low. In the case where the reaction temperature is less than 60°C, the catalyst cannot be activated and the polymerization reaction does not take place. The polymerization reaction in the present invention is usually effected without the use of the solvent, but, for the purpose of controlling the heat of reaction, the polymerization may be performed by adding some solvent. To give instances of solvent suitable for this purpose, there are n-pentane, isooctane, trichloroethane, tetrachloroethane, etc., and the appropriate weight of such solvents to be added relative to the feed olefin is in the range of from 0.5 – 4 times that of the feed olefin. In this connection, as the means of controlling the heat of reaction on the occasion of performing the reaction without the use of solvent, a method of gradually adding the feed olefin or a catalyst, a method of forcibly cooling by outside heat-exchange, and the like, are adopted. After the reaction is over, the reacted solution is settled, whereby the catalyst is separated. The thus separated catalyst can be reused as it is, but as there are instances where a small amount of the catalyst ingredient is contained in the polymerized liquid, that is, the reaction product, forming the upper layer, it may be necessary to perform the decomposition of the catalyst. For the purpose of this decomposition of catalyst, an alcohol or alkaline aqueous solution is generally used, but the application of ammonia will also do.

A liquid polymer thus obtained has properties well satisfying the requirements for lubricating oils, and is sufficiently servable as a substitute for squalene, pristane, etc. known as ingredients for cosmetics and medical supplies. Further, in the case of applying this liquid polymer as a much more highgrade lubricating oil, it will do to remove the unreacted olefins and olefin dimers, which are contained in by a small amount but which are undesirable from the view point of the efficiency of lubricating oil, through such operations as distillation, extraction, and the like. And, in order to improve the thermal stability of this liquid polymer, it will do to hydrogenate the double bonds remaining therein a little. The hyrogenation for this purpose may be easily performed by means of an ordinary hydrogenating catalyst.

As discussed above, the present invention is to provide a method of polymerizing olefins having 6 or more carbon atoms by the use of an active catalyst having a specific composition, which method renders it possible to obtain a hydrocarbon liquid polymer having a relatively low viscosity and high viscosity index.

Generally speaking, olefins having 6 or more carbon atoms can be easily polymerized by means of a cationic polymerization catalyst such as aluminum chloride, but in the case where the polymerization is performed at a reaction temperature in the range of from 30° to 100°C, the viscosity of the resulting polymerized oil after removing the unreacted olefins and olefin dimers comes to be in the range of from 150 to 200 centipoises at 100°F, so that a polymerized oil with low viscosity grade (e.g., 2.5 to 50 centipoises at 100°F) in great demand for use in gas turbines and the like cannot be obtained. While, in the case where the polymerization is performed at a high reaction temperature, for instance, in the range of from 150° to 200°C, a polymerized oil with a viscosity of 40 to 70 centipoises can be obtained due to chain transfer reaction, but there concurrently occurs the skeletal-isomerization reaction attributable to said high temperature, entailing a remarkable lowering of the viscosity index, and the product is disqualified for use as a high-grade synthetic lubricating oil base.

According to the method of the present invention, however, a polymerized oil having a low viscosity and high viscosity index can be obtained; for instance, when the polymerization of olefins having 6 or more carbon atoms is effected at a temperature of 120° to 130°C by applying a specific catalyst employed in the present invention, there can be obtained polymerized oils having a viscosity index of 130 or thereabouts and a viscosity in the range of from 20 to 25 centipoises (at 100°F). In this connection, when the same feed olefins are polymerized at the same reaction temperature as above by applying a catalyst ingredient prepared from aluminum chloride and olefin catalyst constituent without adding any ester, ether or alcohol thereto, there are obtained polymerized oils with a low-grade viscosity, but the viscosity index thereof is 120 or thereabouts and the viscosity is in the range of from 20 to 25 centipoises (at 100°F); that is, the viscosity index tends to decrease.

The catalyst ingredient for use in the present invention, to wit, an active catalyst ingredient prepared by heating a mixture of olefin catalyst constituent, aluminum chloride, ketone having 4 or more carbon atoms, and ether, ester or alcohol at a temperature of more than 60°C is a granular solid, so that it is easy to separate the catalyst by settling, and as the catalytic activity thereof is durable, it facilitates successive polymerization by the use of a fixed bed or fluid bed. The structure of this catalyst ingredient is yet to be clarified, but in the light of the fact that an active granular catalyst cannot be prepared by merely heating a mixture of ketone and aluminum chloride, and, even when olefin catalyst constituent is added thereto, an active ingredient is not formed if the temperature for activation is less than 60°C or the amount of ketone is excessive, the present catalyst ingredient is hardly considered to be a mere complex of ketone and aluminum chloride. Therefore, judging from the facts that the present granular catalyst is repeatedly reusable as it is and that the catalytic activity thereof is promoted by the addition of ester, ether or alcohol, it is likely that said granular catalyst becomes a catalyst ingredient having several active points through some complicated reaction process as seen in the case of a solid acid catalyst and the feed olefin gets regularly polymerized at these active points or gets separated upon growing to a fixed molecular weight, whereby there is obtained a polymerized oil having a low viscosity and high viscosity index.

DESCRIPTION OF THE PREFERRED EMBODIMENTS

EXAMPLE 1

A 1 l glass autoclave with stirrer was charged with 6.8 g of methyl ethyl ketone, 12 g of aluminum chloride and 0.4 g of ethyl acetate (0.05 mole per mole of aluminum chloride), and the aluminum chloride was dissolved. Next, 600 g of a mixture of α-olefins having 6 carbon atoms, 8 carbon atoms and 10 carbon atoms, respectively (mixing ratio = 1:1:1 by weight) were added to the stock, and 6 hours' polymerization reaction was effected at 100°C. Subsequently, ammonia gas was blown into the polymerization product thereby to inactivate the catalyst and the thus separated catalyst was recovered through filtration. Thereafter, the polymerization product was subjected to distillation thereby to remove the unreacted olefins and olefin dimers therefrom. The yield of the resulting liquid polymer was 75%, the viscosity at 100°F was 27 centistokes (cst), and the viscosity index was 132.

Further, varieties of liquid polymers were produced in the same way as above except for replacing said ethyl acetate with 0.33 g of diethyl ether, 0.21 g of ethanol and 0.4 g of ethoxy acetate, respectively, and modifying the amount of said ethyl acetate from 0.4 g to 0.8 g. The results of the respective polymerizations was as shown in the following table.

|  | Yield | Viscosity at 100°F | Viscosity index |
|---|---|---|---|
| in case of application of diethyl ether | 71% | 26 cst | 130 |
| in case of application of ethanol | 80% | 24 cst | 128 |
| in case of application of ethoxy acetate | 78% | 24 cst | 132 |
| in case of application of 0.8 g of ethyl acetate | 72% | 24 cst | 132 |

EXAMPLE 2

A liquid polymer was produced in the same way as in Example 1 except for employing 600 g of hexene-1 as the feed olefin. The yield of this liquid polymer was 80% and the viscosity at 100°F was 14 cst. When this liquid polymer was further subjected to 3 hours' hydrogenation at a temperature of 150°C and under the hydrogen pressure of 20 kg/cm$^2$ by the use of Raney nickel catalyst, there was obtained a hydrogenated oil having properties equal to squalene in cosmetic grade and qualified for use as the base of cosmetics.

EXAMPLE 3

A liquid polymer was produced in the same way as in Example 1 except for employing 600 g of a mixture of α-olefins having 8 carbon atoms and 10 carbon atoms, respectively (mixing ratio = 1:1 by weight) as the feed olefin. The yield of this liquid polymer was 77%, and the viscosity thereof at 100°F was 30 cst.

When this liquid polymer was subsequently subjected to 3 hours' hydrogenation at a temperature of 150°C and under the hydrogen pressure of 20 kg/cm² by the use of Raney nickel catalyst, the resulting hydrogenated oil was qualified for use as the base of a high-grade lubricating oil (viscosity at 100°F: 31 cst, viscosity index: 140, flash point: 440°F, fire point: 480°F, pour point: −80°F).

COMPARATIVE EXAMPLE 1

After charging a 1 l glass autoclave with stirrer with 100g of polyolefin oil (viscosity at 100°F: 40 cst) synthesized in advance and 6.0 g of aluminum chloride, 600 g of a mixture of α-olefins having 6 carbon atoms, 8 carbon atoms and 10 carbon atoms, respectively (mixing ratio = 1:1:1 by weight) were gradually dropped therein. The dropping took 3 hours.

After completing said dropping, 1 hour's aging was effected, ammonia was then blown into the autoclave thereby to inactivate the catalyst, and the separated catalyst was removed through filtration. When the polymerization product was subjected to distillation subsequent thereto to remove the unreacted olefins and olefin dimers, the yield of the resulting polymerized oil was 80%, the viscosity at 100°F was 60 cst, and the viscosity index was 85.

What is claimed is:

1. A method of polymerizing feed olefins having at least 6 carbon atoms or mixtures of such feed olefins, to produce a hydrocarbon liquid polymer, which comprises: polymerizing said feed olefin at a temperature of more than 60°C, in contact with a catalyst prepared by reacting at a temperature of more than 60°C, catalyst constituents consisting essentially of (a) aluminum chloride, (b) ketone having at least 4 carbon atoms, (c) olefin catalyst constituent selected from the group consisting of said feed olefin and olefins of lower carbon atom number, and (d) ester, ether or alcohol, the amount of (a) being from 0.1 to 5 mole percent based on the feed olefin, the molar ratio of (a)/(b) being from 1/1 to 1/1.2, the amount of (c) being more than 1 mole percent based on (a) and the amount of (d) being from 0.01 to 0.3 mole per mole of (a).

2. A method according to claim 1, wherein said feed olefin is selected from the group consisting of olefins having 8 to 10 carbon atoms and mixtures thereof.

3. A method according to claim 1, wherein said ketone (b) is selected from the group consisting of methyl ethyl ketone, diethyl ketone, diisobutyl ketone, dioctyl ketone and cyclohexanone.

4. A method according to claim 1, wherein the amount of said ketone (b) is in the range of from 1.02 to 1.10 mole, per mole of aluminum chloride (a).

5. A method according to claim 1, wherein said olefin catalyst constituent (c) is the feed olefin itself.

6. A method acccording to claim 1, wherein said catalyst constituent (d) is selected from the group consisting of alkyl esters of fatty acids, said esters having less than 10 carbon atoms, alkyl ethers having less than 10 carbon atoms, and monohydric or polyhydric alcohols having less than 10 carbon atoms.

7. A method according to claim 1, wherein the amount of said aluminum chloride (a) is in the range of from 1.0 to 3.0 mol.%, relative to the feed olefin.

8. A method according to claim 1, wherein the polymerization temperature is in the range of from 60° to 200°C.

9. A method according to claim 1, wherein the polymerization reaction is effected while controlling the heat of reaction by adding a solvent.

10. A method according to claim 9, wherein said solvent is selected from the group consisting of n-pentane, isooctane, trichloroethane and tetrachloroethane.

11. A method according to claim 9, wherein the weight of said solvent is in the range of from 0.5 to 4 times that of the feed olefin.

12. A method according to claim 1 wherein ammonia is introduced into the polymer reaction product thereby to decompose the catalyst dissolved in said polymer reaction product.

13. A method according to claim 1, wherein unreacted olefins and olefin dimers contained in the polymer reaction product are removed by means of a distillation process or extraction process.

14. A method according to claim 1, wherein the double bonds remaining in the polymer reaction product are hydrogenated.

* * * * *